(12) United States Patent
Kosecoff

(10) Patent No.: US 11,790,750 B2
(45) Date of Patent: Oct. 17, 2023

(54) SYSTEMS AND METHODS FOR MEASURING AIR QUALITY

(71) Applicant: L'OREAL, Paris (FR)

(72) Inventor: David B. Kosecoff, San Francisco, CA (US)

(73) Assignee: L'OREAL, Paris (FR)

( * ) Notice: Subject to any disclaimer, the term of this patent is extended or adjusted under 35 U.S.C. 154(b) by 662 days.

(21) Appl. No.: 17/039,665

(22) Filed: Sep. 30, 2020

(65) Prior Publication Data

US 2022/0096001 A1   Mar. 31, 2022

(51) Int. Cl.
| | | |
|---|---|---|
| *G08B 21/12* | (2006.01) | |
| *A61Q 17/04* | (2006.01) | |
| *A61B 5/00* | (2006.01) | |
| *G16H 20/13* | (2018.01) | |
| *G08B 21/02* | (2006.01) | |

(52) U.S. Cl.
CPC .............. *G08B 21/02* (2013.01); *A61B 5/746* (2013.01); *A61Q 17/04* (2013.01); *G16H 20/13* (2018.01); *A61K 2800/87* (2013.01)

(58) Field of Classification Search
CPC ....... G08B 21/12; A61B 5/746; A61B 5/1112; A61B 5/6824; A61B 5/6831; A61B 2560/0242; A61Q 17/04; A61Q 19/00; G16H 20/13; G16H 40/67; G16H 50/30; A61K 2800/87; A61K 8/35; A61K 8/36; A61K 8/676; A61K 8/678; A61K 2800/805

See application file for complete search history.

(56) References Cited

U.S. PATENT DOCUMENTS

| | | | |
|---|---|---|---|
| 8,652,040 B2 | 2/2014 | LeBoeuf et al. | |
| 10,725,002 B2 * | 7/2020 | Roseway | G01N 31/224 |
| 2015/0041663 A1 * | 2/2015 | Oliver | G01W 1/00 |
| | | | 250/372 |
| 2016/0066848 A1 * | 3/2016 | Klosinski, Jr. | A61B 5/0205 |
| | | | 600/301 |
| 2017/0191866 A1 | 6/2017 | Balooch et al. | |
| 2018/0120274 A1 * | 5/2018 | Roseway | G01N 31/224 |
| 2019/0204146 A1 * | 7/2019 | Wei | G01J 1/0219 |
| 2021/0151195 A1 * | 5/2021 | Hayward | G06Q 50/16 |

OTHER PUBLICATIONS

Md Abdulla Al Mamun, et al., "Sensor and Systems for Wearable Environmental Monitoring Toward IoT-Enabled Applications: A Review," IEEE Sensors Journal, vol. 19, No. 18, <http://www.ieee.org/publications_standards/publications/rights/index/html>, Sep. 15, 2019, 18 pages.
Padron, et al., "Design, Development and Initial Validation of a Wearable Particulate Matter Monitoring Solution," ICOST 2019, LNCS 11862, <https://doi.org/10.1007/978-3-030-32785-9_17>, Oct. 7, 2019, 7 pages.
Preliminary Search Report, French Patent Application No. 2012661, dated Jul. 20, 2021.

* cited by examiner

*Primary Examiner* — Mohammad K Islam
(74) *Attorney, Agent, or Firm* — Christensen O'Connor Johnson Kindness PLLC

(57) ABSTRACT

A method of determining a user's exposure to pollution, the method comprising sensing environmental conditions by a detector device, transmitting sensed environmental conditions data from the detector device to a smart device, and alerting the user about personal pollutant exposure by the smart device.

19 Claims, 8 Drawing Sheets

SYSTEMS AND METHODS FOR MEASURING AIR QUALITY

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Gathering information about exposure to environmental pollutants is increasingly important for multiple reasons. For example, in many cases, it is in the interest of employers to know how their employees are being affected by the pollutants at their work, because the employers may be responsible for protecting the employees from the pollutants. As another example, individuals may desire information regarding exposure to environmental pollutants in order to take steps to mitigate the effects of such exposure, including but not limited to avoiding further exposure and using products such as skincare products that can reduce the harmful effects of the exposures.

As technology progresses, it may be too impractical to have a large range of sensors incorporated onto pollutant detectors. Furthermore, while existing web-based simulation models can generate an estimated level of exposure to a variety of pollutants within a given area, individuals may be more interested in knowing their personal exposure to pollutants. Therefore, systems and methods are needed for improved personal pollutant exposure readings.

In one embodiment, a method of determining a user's exposure to pollution includes: sensing environmental conditions by a detector device; transmitting sensed environmental conditions data from the detector device to a smart device; and alerting the user about personal pollutant exposure by the smart device.

In one aspect, the method also includes: inputting the sensed environmental conditions data from the smart device into a web-based simulation model; and updating the web-based simulation model based on the sensed environmental conditions data from the smart device. In another aspect, updating the web-based simulation model includes interpolating the web-based simulation model of the pollution exposure levels based on the sensed environmental conditions data from the detector device.

In one aspect, the method also includes transmitting a user's GPS location to the web-based simulation model. In another aspect, interpolating the web-based simulation model of the pollution exposure levels is at least in part based on the user's GPS location.

In one aspect, the detector device is wearable. In another aspect, the wearable detector device is attached to a wrist of a user with a strap or attached to clothing of the user with a clip. In one aspect, the detector device is carried by the user.

In one aspect, at least one of the sensed environmental conditions is a nitrogen dioxide exposure. In another aspect, at least one of the sensed environmental conditions is a carbon monoxide exposure, a sulfur dioxide exposure, a particulate matter sensor exposure, or a hydrogen sulfide exposure.

In one aspect, the detector device is attached to a cosmetic product.

In one aspect, the method also includes prompting the user, by the smart device, to apply the cosmetic product when the user's personal pollutant exposure reaches a pre-determined threshold. In one aspect, the user's personal pollutant exposure threshold is pre-determined by the detector device. In one aspect, the user's personal pollutant exposure threshold is selected by the user.

In one aspect, the cosmetic product includes an applicator configured to dispense an additive. In another aspect, the applicator includes a dispenser. In one aspect, the dispenser is a sprayer.

In one aspect, the additive is a countervailing substance that offsets the harmful effects of environmental pollution. In one aspect, the additive is a vitamin. In another aspect, the additive is a sunscreen. In one aspect, the method also includes alerting the user to dispense the additive when the user's personal pollutant exposure reaches a certain threshold.

BRIEF DESCRIPTION OF THE DRAWINGS

The foregoing aspects and many of the attendant advantages of this inventive technology will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the inventive technology.

In some embodiments, the inventive concept includes a detector device with at least one sensor that detects at least one environmental condition. In some embodiments, the detector device senses levels of specific pollutants, such as nitrogen dioxide or carbon monoxide, that correlate to a wider range of pollutants such as PM2.5, PM10, SO2, and O3. In some embodiments, the detector device transmits data from the sensors to a smart device. The data is input into a web-based simulation model and used as interpolation points to correct and refine the pollution exposure generated by the web-based simulation model. In some embodiments, the smart device inputs additional data into the web-based simulation model, such as the user's GPS coordinates.

In some embodiments, the detector device is wearable. In some embodiments, the detector device is carried by a user.

In other embodiments, the detector device is attached to a cosmetic product, where the smart device issues a recommendation to the user to apply the cosmetic product based on the user's personal pollutant exposure. In some embodiments, the cosmetic product has an applicator with a dispenser for dispensing an additive. In some embodiments, the additive is a countervailing substance, such as a vitamin, that may offset the negative effects of exposure to pollutants.

Figure 1:
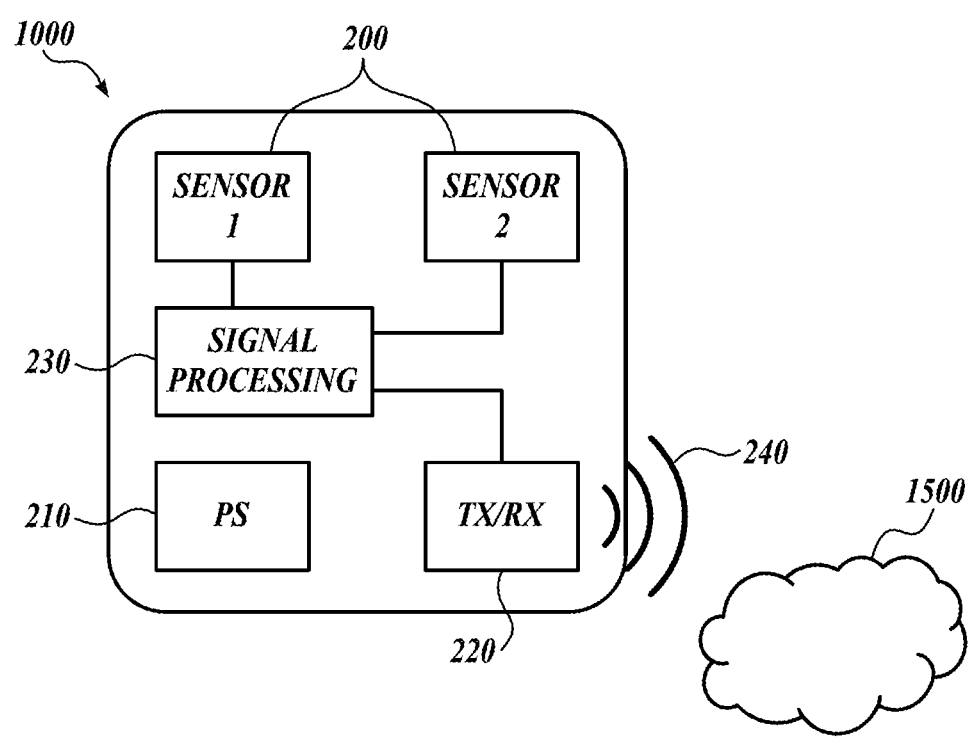
FIG. 1 is a schematic diagram of an example detector device in accordance with the present technology.

FIG. 1 is a schematic diagram of an example detector device 1000 in accordance with the present technology. The example detector device 1000 includes at least one sensor 200, a signal processor 230, a power source (PS) 210, and a transceiver (TX/RX) 220. The transceiver 220 may send a wireless signal 240 to a web-based simulation model 1500.

For simplicity, the illustrated embodiment includes two sensors 200, but in other embodiments, the detector device 1000 can have any other number of sensors 200 configured to sense one or more environmental conditions. Some non-limiting examples of sensors 200 include, but are not limited to, a nitrogen dioxide (NO2) sensor, a carbon monoxide (CO) sensor, a lead sensor, a sulfur dioxide (SO2) sensor, a particulate matter sensor (including but not limited to a PM2.5 sensor), a UV sensor, a temperature sensor, a humidity sensor, an ambient pressure sensor, a radon sensor, an ozone sensor, a volatile organic component (VOC) sensor, an air quality index (AQI) sensor, an ethanol sensor, a sulfide gas sensor, an indoor air quality (IAQ) sensor, and a hydrogen sulfide (H2S) sensor. In some embodiments, the sensors 200 may be operable at multiple different power consumption levels. In some embodiments, the sensor 200 may be configurable to be deactivated or otherwise placed in a minimal power consumption state when not collecting samples.

In some embodiments, the sensors are constructed as Metal-Oxide, Hybrid Metal-Oxide, Electrochemical, MEMS, LED Scattering, Laser Scattering, or Fuel Cell sensors. In some embodiments, the construction of the sensors 200 can be determined depending on the type of pollutant to be detected, the form-factor, the desired accuracy, the desired lifetime, and/or the desired power consumption of the detector device 1000.

In some embodiments, the web-based simulation model 1500 uses 3D map data (i.e. building dimensions) along with regional real-time data from Federal-grade air quality monitors that measure temperature, humidity, wind speed, wind direction, and concentrations of a wide range of pollutants. Based on such measurements, the user's exposure to a wide range of pollutants such as PM2.5, PM10, SO2, H2S, and O3 may be calculated and/or predicted. A non-limiting example of such web-based simulation model 1500 is the University of North Carolina's C-REAL tool. In some embodiments, the web-based simulation model 1500 receives additional data from a connected smart device (such as a smart device 4000 in FIG. 4). In some embodiments, the additional data may be the user's GPS location.

In operation, the sensors 200 sense the levels of a subset of environmental pollutants. The signal processor 230 receives signals (measurements) generated by the sensors 200 and passes these signals to the transceiver 220. The transceiver 220 then sends data as a wireless signal 240 to the web-based simulation model 1500. In some embodiments, the data generated by the sensors 200 serve as interpolation points to correct and refine the pollutant exposure predicted by the web-based simulation model 1500. In some embodiments, the detector device 1000 alerts the user about their personal pollutant exposure.

Figure 2A:
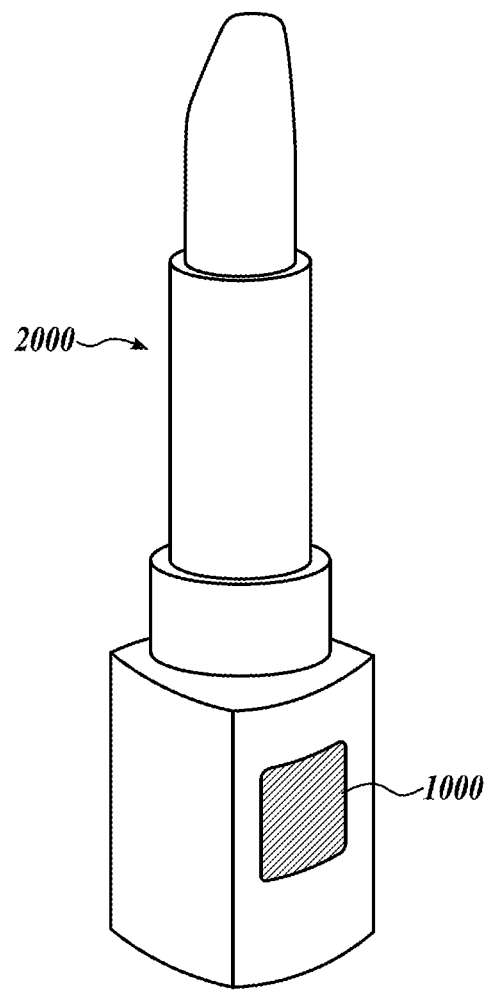
FIG. 2A is a schematic diagram of an example detector device incorporated onto a cosmetic product in accordance with the present technology.
Figure 2B:
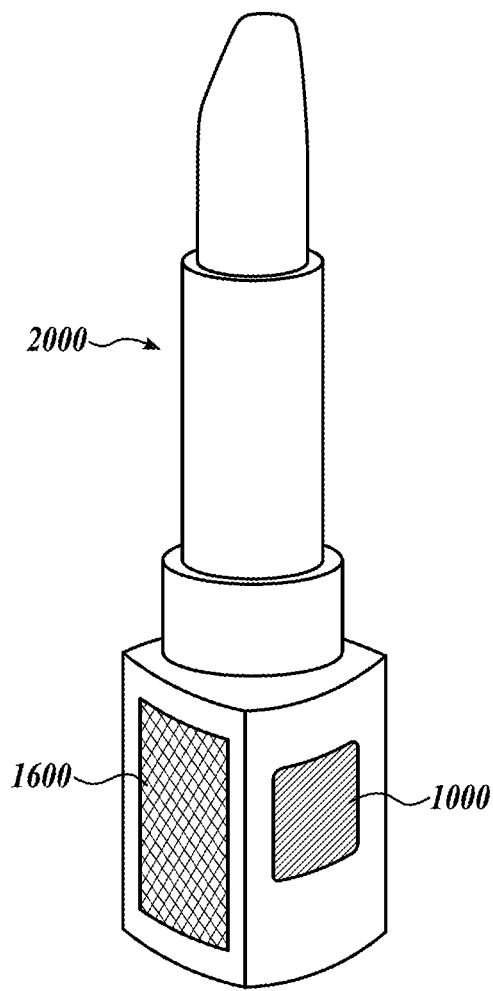
FIG. 2B is a schematic diagram of an example detector device and applicator incorporated onto a cosmetic product in accordance with the present technology.
Figure 2C:
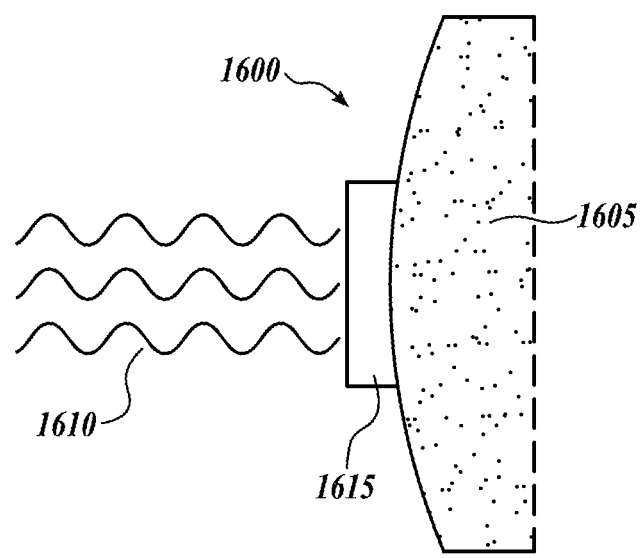
FIG. 2C is an example applicator on a cosmetic product in accordance with the present technology.

FIGS. 2A-2C are examples of a detector device 1000 incorporated onto a cosmetic product 2000 in accordance with the present technology. For simplicity, the cosmetic product 2000 is illustrated as a lipstick, but in other embodiments, the cosmetic product 2000 is a skincare product, a makeup product, a haircare product, etc.

FIG. 2A is a schematic diagram of an example detector device 1000 incorporated onto a cosmetic product 2000 in accordance with the present technology. In some embodiments, the detector device 1000 is a component of the cosmetic product 2000. In other embodiments, the detector device 1000 is attached to the cosmetic product 2000 by a user. The cosmetic product's 2000 packaging is illustrated as a lipstick tube, but in other embodiments, the cosmetic product's 2000 packaging could be any cosmetic packaging, such as a jar, bottle, pot, etc. In operation, when the user holds the cosmetic product 2000, the detector device 1000 senses a range of airborne pollutants and sends the sensed data to a smart device (not pictured in FIGS. 2A-2C). The smart device inputs the data to a web-based simulation model (such as a web-based simulation model 1500) through a wired or/and wireless communication. As further explained with respect to FIGS. 3-6 below, a user's personal pollutant exposure is generated by interpolating the data from the detector device 1000 into a web-based simulation model. In some embodiments, the smart device alerts the user to their personal pollutant exposure. In some embodiments, the smart device recommends that the user apply the cosmetic product 2000 to, for example, mitigate the effect of the exposure to pollutants.

FIG. 2B is a schematic diagram of an example detector device 1000 and applicator 1600 incorporated onto a cosmetic product 2000 in accordance with the present technology. In some embodiments, the cosmetic product 2000 includes an applicator 1600. The applicator 1600 is configured to dispense an additive such as a sunscreen or a vitamin. In some embodiments, the additive is a countervailing substance that offsets the harmful effects of environmental pollution. In some embodiments, the applicator 1600 is operationally coupled to the detector device 1000. In some embodiments, the applicator 1600 dispenses the countervailing substance when the user's pollution exposure reaches a pre-determined threshold of exposure. In other embodiments, the user is alerted by the detector device 1000 to apply the additive with the applicator 1600 when the user's pollution exposure reaches a pre-determined threshold of exposure. In some embodiments, the countervailing substance is recommended when a specific pollutant reaches a pre-determined threshold of exposure. For example, Ozone pollution oxidizes lipids, depletes the skin's natural antioxidant reservoir, activates inflammatory pathways, and causes collagen degradation. Furthermore, particulate matter 2.5 damages skin cells by inducing oxidative stress, subcellular organelle dysfunction, and apoptosis. These reactions may result in premature skin aging. The application of Vitamin C, Vitamin E, antioxidant Phloretin, and antioxidant Ferulic Acid may be used as useful anti-aging treatments in reducing the severity of these reactions. In other embodiments, different products having different makeups of these ingredients, the types and levels of may be used, depending on the type of and severity of pollution exposure.

In other embodiments, the applicator 1600 is communicatively coupled to a smart device. The smart device may alert the user to their personal pollutant exposure and/or recommend that the user applies the additive.

FIG. 2C is an example applicator 1600 on a cosmetic product 2000 in accordance with the present technology. The applicator 1600 includes a reservoir 1605 and a dispenser 1615. In some embodiments, the dispenser 1615 is a sprayer. In other embodiments, the dispenser 1615 is an atomizer, nozzle, roll-on mechanism, etc.

In operation, the reservoir 1605 holds an additive. The dispenser 1615 dispenses a stream of additive (also referred to as a countervailing substance, countervailing product or a countervailing additive) 1610 from the reservoir 1605. The user may dispense the stream of additive 1610 to a biological surface, such as skin or hair. The user may be prompted by the detector device 1000 or a communicatively coupled smart device to apply the stream of additive 1610 based on the user's personal pollutant exposure.

Figure 3:
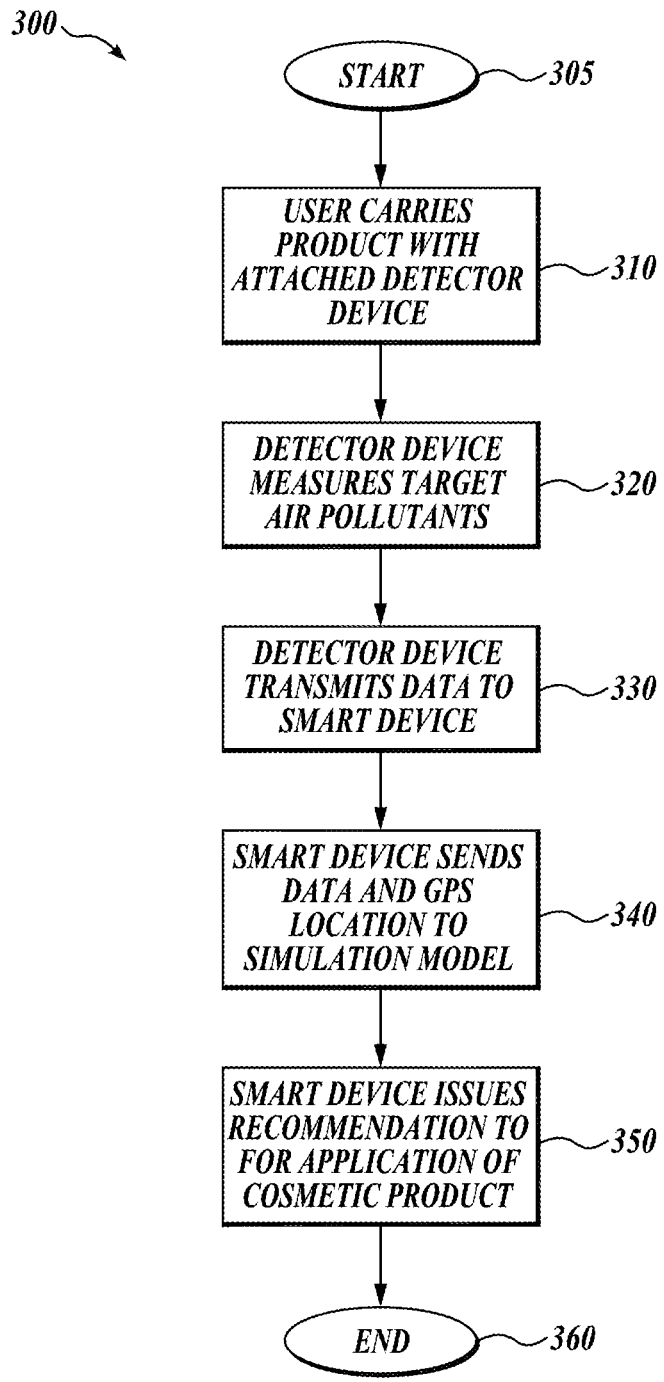
FIG. 3 is a flowchart of a method of calculating and refining a personal pollutant exposure and applying a cosmetic product in accordance with the present technology.

FIG. 3 is a flowchart of a method 300 of calculating and refining a personal pollutant exposure and applying a cosmetic product in response in accordance with the present technology. In some embodiments, the method 300 may include additional steps or may be practiced without all the steps illustrated in the flow chart.

The method 300 may begin at block 305. In block 310, the user holds the cosmetic product (such as a cosmetic product 2000) with the attached detector device (such as a detector device 1000). In different embodiments, the detector device may be attached to user's clothing, purse, jewelry, etc. In block 320, the detector device measures target air pollutants. In some embodiments, the target air pollutants are NO2 and CO. In block 330, the detector device transmits the target pollutant data to a smart device (such as a smart device 4000 in FIG. 4). In block 340, the smart device sends the data from the detector device and the user's GPS location to a web-based simulation model (such as a web-based simulation model 1500). In some embodiments, the web-based simulation model uses the data from the detector device as interpolation points for a given GPS location, as described in more detail in FIG. 6 below. In block 350, the smart device issues a recommendation to the user for application of the cosmetic product. In some embodiments, the smart device issues a recommendation for application of an additive (e.g., a countervailing substance) from an applicator (such as an applicator 1600). In some embodiments, the applicator dispenses a stream of additive (such as a stream of additive 1610) when the web-based simulation model calculates or predicts an exposure higher than a certain threshold. In some embodiments, this pre-determined threshold is hard coded into the applicator. In other embodiments, the user may set a pollutant exposure threshold. The method 300 may end in block 360.

Figure 4:
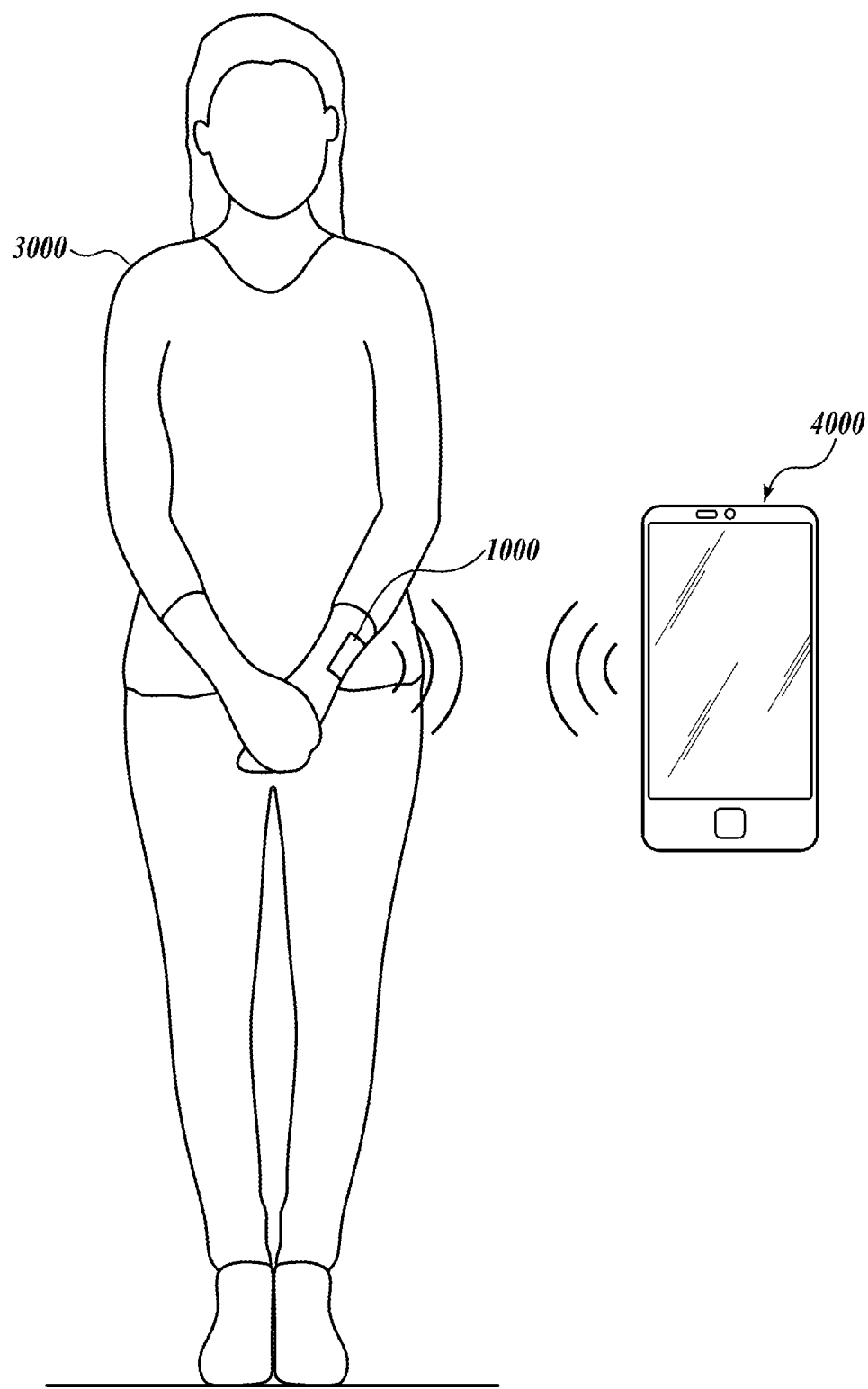
FIG. 4 is an example interaction between a detector device and a smart device in accordance with the present technology.

FIG. 4 is an example interaction between a detector device 1000 and a smart device 4000 in accordance with the present technology. In some embodiments, the detector device 1000 is a wearable device. In some embodiments, the detector device 1000 has a strap and is mounted to a wrist of a user 3000, like a watch. In other embodiments, the detector device 1000 may be mounted to the user's clothing with a clip, a patch or similar attachment. In some embodiments, the detector device 1000 is a fob, ID tag, pin, zipper pull, or other form factor that a user 3000 may wear as a necklace or attached to clothing. In some embodiments, the detector device 1000 may be in a form factor designed to be carried rather than worn by the user 3000, such as a case for a mobile phone, or an attachment for a backpack or briefcase.

In operation, the detector device 1000 is in communication with a smart device 4000. For simplicity, the smart device 4000 is illustrated as a smart phone, but in other embodiments, the smart device 4000 takes the form of any number of other computing devices such as a smart watch, a tablet, and the like.

In some embodiments, the detector device 1000 reports the environmental conditions to the smart device 4000. In some embodiments, the detector device 1000 may include one or more sensors 200 (not illustrated in FIG. 4) for sensing environmental conditions near the detector device 1000. The detector device 1000 and the smart device 4000 may communicate using any suitable communication technology, including but not limited to wireless technologies such as Bluetooth, 2G, 3G, 4G, 5G, LTE, Wi-Fi, WiMAX, and infrared; wired technologies such as USB, Ethernet, FireWire, and Lightning; or combinations thereof. The communication between the detector device 1000 and the smart device 4000 is typically a low-powered communication in order to reduce battery consumption on both the detector device 1000 and the smart device 4000.

In some embodiments, the smart device 4000 includes sensors capable of detecting the position of the detector device 1000. In some embodiments, the smart device 4000 includes sensors capable of detecting the position of the smart device 4000. In some embodiments, the position of the smart device 4000 may be used as a proxy for the position of the detector device 1000.

In operation, the detector device 1000 is worn by the user 3000. The detector device 1000 reports at least one environmental condition to the smart device 4000. The smart device 4000 inputs the sensed data from the detector device 1000 into a web-based simulation model. In some embodiments, the smart device 4000 inputs additional data, such as the user's GPS location. In some embodiments, the smart device 4000 alerts the user 3000 to their personal pollutant exposure. In some embodiments, the smart device 4000 alerts the user 3000 to their personal pollutant exposure if it reaches a certain threshold of an environmental pollutant. In some embodiments, the threshold is hardcoded into the smart device 4000 or the detector device 1000. In other embodiments, the threshold is selectable by the user 3000.

Figure 5:
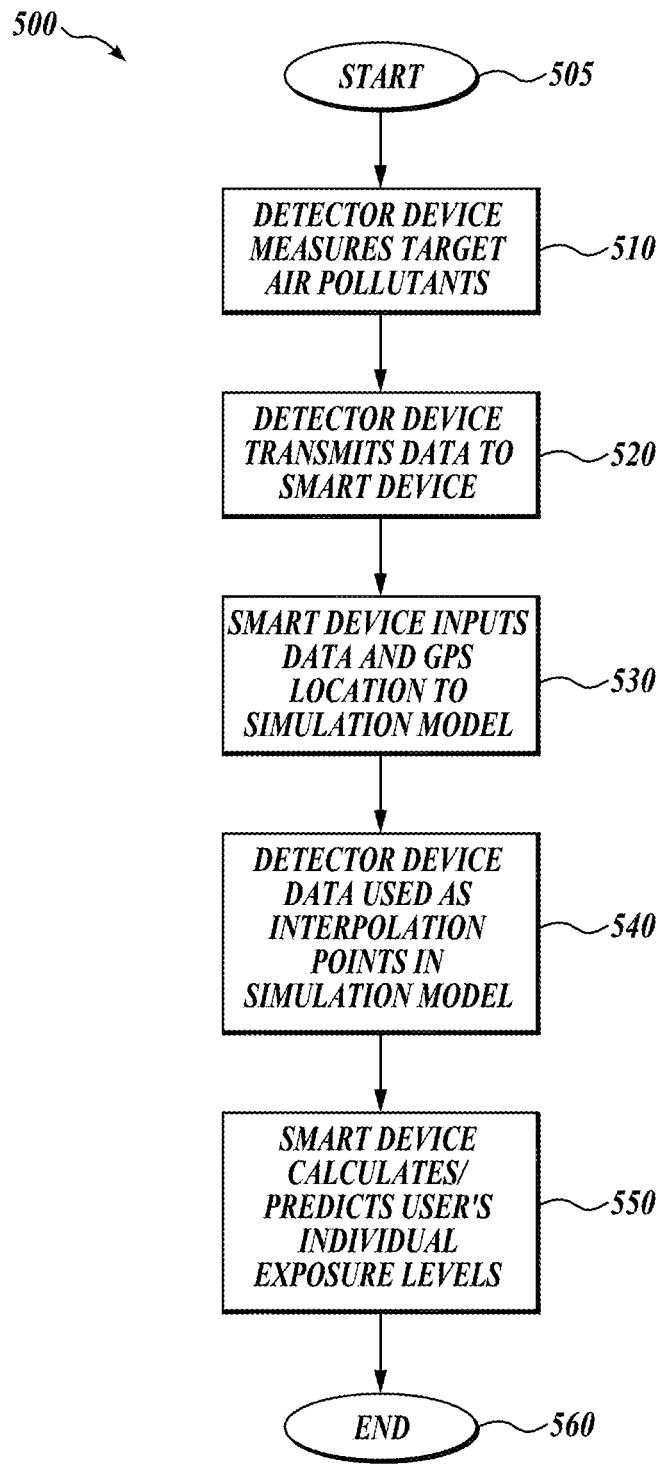
FIG. 5 is a flowchart of a method of refining an estimate of user's personal pollutant exposure in accordance with the present technology.

FIG. 5 is a flowchart of a method 500 of calculating and refining a user's personal pollutant exposure in accordance with the present technology. In some embodiments, the method 500 may include additional steps or may be practiced without all steps illustrated in the flow chart.

The method 500 may begin at block 505. In block 510, a detector device (such as a detector device 1000) measures a target set of pollutants. In some embodiments, the target set of pollutants may include air pollutants such as NO2 and CO. In block 520, the detector device transmits the data generated by sensing the target set of air pollutants and transmits the data to a smart device (such as a smart device 4000). In block 530, the smart device sends this data and the user's GPS location to a web-based simulation model (such as a web-based simulation model 1500). In block 540, the detector device data is used as interpolation points in the web-based simulation model. In bock 550, the smart device calculates or predicts the user's individual exposure levels. In some embodiments, the smart device calculates the user's individual exposure levels to a wider range of pollutants such as PM2.5, PM10, and O3. The method 500 may end in block 560.

Figure 6:
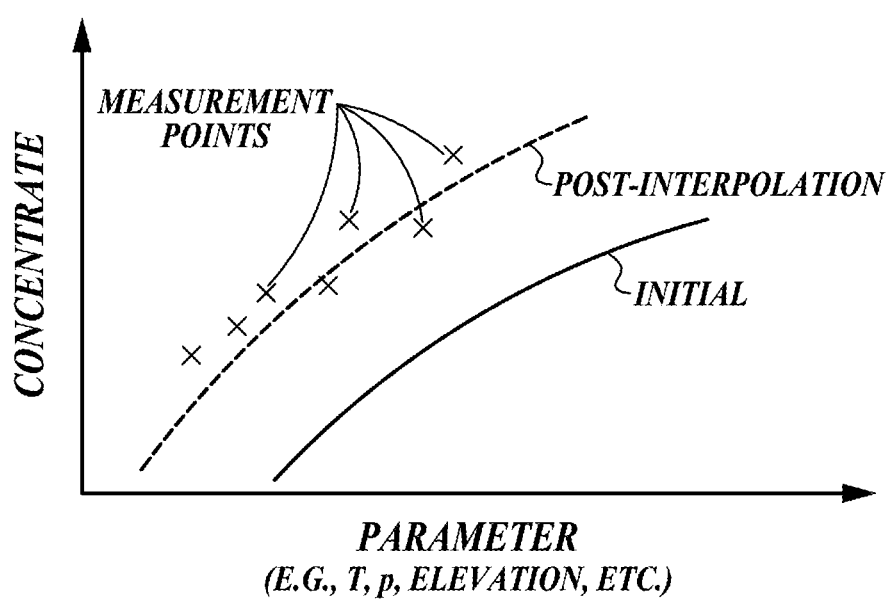
FIG. 6 is a graph of example data from a detector device being used to improve a web-based simulation model in accordance with the present technology.

FIG. 6 is a graph of example data from a detector device being used as interpolation points for a web-based simulation model in accordance with the present technology. On the horizontal axis is the parameter being measured, such as temperature (T), pollutant (p), elevation, etc. On the vertical axis is the concentration of the parameter. The line labeled "initial" corresponds to a pollutant exposure generated by a web-based simulation model (such as a web-based simulation model 1500). The crosses labeled "measurement points" are individual measurements generated by a detector device (such as sensors 200 of the detector device 1000). In some embodiments, the measurements from the detector device are of a small range of pollutants, such as NO2 and CO that correlate to a wider range of pollutants such as PM2.5, PM10, and O3. The measurements serve as interpolation points to correct and refine a user's personal pollutant exposure. The line labeled "post-interpolation" is generated by interpolating the measurement points with the initial exposure levels generated by the web-based simulation model. For example, the web-based simulation model 1500 may generate a new set of CO concentration estimates for a given location based on a relatively limited number of CO concentration data received from one or more users. As another example, the web-based simulation model 1500 may generate new set of NOX estimates based on the above CO measurements and generally known correlations between the CO and NOX pollution levels. As yet another example, the web-based simulation model 1500 may adjust the PM10 concentration estimates for a given elevation level based on the PM10 concentration measurements of the users at certain elevation parameters, as provided by the users' GPS.

In some embodiments, the user is alerted to their post-interpolation pollutant exposure. In some embodiments, an additive is dispensed via an applicator (such as an applicator 1600) in response to such post-interpolation pollutant alert. In some embodiments, the user is given a recommendation to apply a cosmetic product (such as a cosmetic product 2000) based on their post-interpolation pollutant exposure levels.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. For example, in some embodiments the counter or controller may be based on a low-power buck regulator connected to a capacitor. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure.

What is claimed is:

1. A method of determining a user's exposure to pollution, the method comprising:
   sensing environmental conditions by a detector device;
   transmitting sensed environmental conditions data from the detector device to a smart device;
   alerting the user about personal pollutant exposure by the smart device; and
   prompting the user, by the smart device, to apply a cosmetic product when the user's personal pollutant exposure reaches a pre-determined threshold,
   wherein the detector device is attached to the cosmetic product.

2. The method of claim 1, further comprising:
   inputting the sensed environmental conditions data from the smart device into a web-based simulation model; and
   updating the web-based simulation model based on the sensed environmental conditions data from the smart device.

3. The method of claim 2, wherein updating the web-based simulation model comprises interpolating the web-based simulation model of the pollution exposure levels based on the sensed environmental conditions data from the detector device.

4. The method of claim 2, further comprising transmitting a user's GPS location to the web-based simulation model.

5. The method of claim 4, wherein interpolating the web-based simulation model of the pollution exposure levels is at least in part based on the user's GPS location.

6. The method of claim 1, wherein the detector device is wearable.

7. The method of claim 6, wherein the wearable detector device is attached to a wrist of a user with a strap, or attached to clothing of the user with a clip or a patch.

8. The method of claim 1, wherein the detector device is carried by the user.

9. The method of claim 1, wherein at least one of the sensed environmental conditions is a nitrogen dioxide exposure.

10. The method of claim 1, wherein at least one of the sensed environmental conditions is a carbon monoxide exposure, a sulfur dioxide exposure, a particulate matter sensor exposure, or a hydrogen sulfide exposure.

11. The method of claim 1, wherein the user's personal pollutant exposure threshold is pre-determined by the detector device.

12. The method of claim 1, wherein the user's personal pollutant exposure threshold is selected by the user.

13. The method of claim 1, wherein the cosmetic product includes an applicator configured to dispense an additive.

14. The method of claim 13, wherein the applicator includes a dispenser.

15. The method of claim 14, wherein the dispenser is a sprayer.

16. The method of claim 13, wherein the additive is a countervailing substance that offsets the harmful effects of environmental pollution.

17. The method of claim 13, wherein the additive is a vitamin.

18. The method of claim 13, wherein the additive is a sunscreen.

19. The method of claim 13, the method further comprising alerting the user to dispense the additive when the user's personal pollutant exposure reaches a certain threshold.

* * * * *